United States Patent [19]

Johnson et al.

[11] Patent Number: 4,985,589

[45] Date of Patent: Jan. 15, 1991

[54] (1S-CIS)-3-(4-HYDROXYPHENYL),5-CYCLOHEXADIENE-1,2-DIOL AND CORRESPONDING ACETATE

[75] Inventors: Bruce F. Johnson, Scotia; Frank J. Mondello, Schenectady, both of N.Y.

[73] Assignee: General Electric Company, Schenectady, N.Y.

[21] Appl. No.: 561,648

[22] Filed: Aug. 1, 1990

Related U.S. Application Data

[62] Division of Ser. No. 453,895, Dec. 20, 1989.

[51] Int. Cl.$^5$ .................... C07C 69/013; C07C 39/17
[52] U.S. Cl. ..................................... 560/130; 568/743
[58] Field of Search ..................... 560/130; 568/743

[56] References Cited

U.S. PATENT DOCUMENTS 4,665,215  5/1987  Davenport ............... 560/130 X
4,873,374  10/1989  Miura et al. ............ 568/743
4,877,907  10/1989  Miura et al. ............ 568/721

Primary Examiner—Werren B. Lone
Assistant Examiner—Vera C. Clarke
Attorney, Agent, or Firm—William A. Teoli; James C. Davis, Jr.; William H. Pittman

[57] ABSTRACT

A method is provided for converting 4-substituted biphenyls, such as 4-hydroxybiphenyl, to the corresponding 3,4'-dihydroxybiphenyl utilizing mutant strains of *Alcaligenes eutrophus* or *Pseudomonas putida*. Hydroxylation of the unsubstituted biphenyl ring to the corresponding (1S-cis)-3-(4-hydroxyphenyl)-3,5-cyclohexadiene-1,2-diol and its conversion to the corresponding triacetate, followed by treatment in base to form 3,4'-dihydroxybiphenyl is also provided.

2 Claims, No Drawings

(1S-CIS)-3-(4-HYDROXYPHENYL),5-CYCLOHEXADIENE-1,2-DIOL AND CORRESPONDING ACETATE

This application is a division of application Ser. No. 453,895, filed Dec. 20, 1989.

BACKGROUND OF THE INVENTION

The present invention relates to a multi-step process for hydroxylating 4-substituted biphenyls to make 4'-substituted-3-hydroxy-biphenyls involving a biological step and chemical steps. More particularly, the present invention relates to the employment of certain mutant strains of *Alcaligenes eutrophus* NRRLB-15940 or *Pseudomonas outida* NRRLB-18064, which perform the biological conversion of 4-substituted biphenyl to the corresponding optically active (1S-cis)-3-(4-substituted phenyl)-3,5-cyclohexadiene-1,2-diol. The acylation of such intermediate and cleavage of the 2-acyloxy group and the 3-proton with bases from the resulting (1S-cis)-3-(4-substituted phenyl)-3,5-cyclohexadiene-1,2-diacylate followed by its hydrolysis, results in the production of the 4'-substituted-3-hydroxybiphenyl.

Prior to the present invention, 4'-substituted-3-hydroxybiphenyls of the formula,

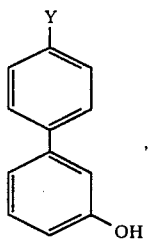

where Y is a member selected from the class consisting of nitro, halo, carboxy and hydroxy and preferably hydroxy, required multi-step chemical procedures which resulted in a low overall yield. Enzymatic hydroxylation of biphenyl and certain 4-substituted biphenyls using whole cells is shown by Ziffer et al., Tetrahedron, 33, 2491 (1977) and Taylor, European Patent Application EP No. 76606A1, Apr. 13, 1983. Masse et al. also refers to the enzymatic treatment of 4-chlorobiphenyl Applied Environmental Microbiology, 47, 947 (1984). Although various chemical and biological procedures have been used to modify 4-substituted biphenyls, satisfactory techniques for making 4'-substituted 3-hydroxybiphenyls of formula (1), particularly where Y is hydroxy, are constantly being sought.

SUMMARY OF THE INVENTION

The present invention is based on the discovery that certain mutants of *Alcaligenes eutrophus* NRRLB-15940 of Bedard, U.S. Pat. No. 4,843,007, referred to hereinafter as strain FM803 and *Pseudomonas putida* NRRLB-18064 of Bopp, U.S. Pat. No. 4,843,009, referred to hereinafter as FM408, can be used with biphenyl substituted in the 4 position, as shown by the formula

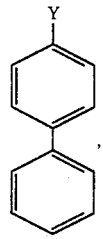

where Y is as defined above, to produce the corresponding (1S-cis)-3-(4-substituted phenyl)-3,5-cyclohexadiene-1,2-diol having the formula,

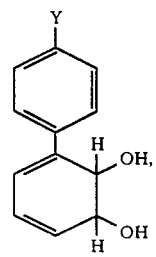

where Y is as previously defined. It has been found that the 4-phenyl-cyclohexadienediol of formula (3) can be readily acylated and the resulting 4-substituted-phenyl-cyclohexadiene-1,2-diacylate can be cleaved with bases to produce the corresponding 4'-substituted-3-acyloxybiphenyl, which thereafter can be hydrolyzed to produce a 4'-substituted-3-hydroxybiphenyl within the scope of formula (1).

STATEMENT OF THE INVENTION

There is provided by the present invention a method for making a 4-substituted-3-hydroxybiphenyl of formula (1) comprising, (A) allowing the incubation of a mixture of a 4-substituted biphenyl of formula (2) and a culture medium of a mutant strain of *Alcaligenes eutrophus* NRRLB-15940, or *Pseudomonas putida* NRRLB-18064 which mutant strains are defective in cis-biphenyldihydrodiol dehydrogenase activity to produce a (1S-cis)-3-(4-substituted biphenyl)-3,5-cyclohexadiene-1,2-diol within the scope of formula (3), (B) recovering the resulting 4-substituted-phenylcyclohexadiene-1,2-diol of (A) and acylating it with a carboxylic acid anhydride to produce the corresponding 4-substituted-phenylcyclohexadiene-1,2-diacylate, (C) effecting the cleavage of the 2-acyloxy anion and 3-proton with base on the cyclohexadiene ring of the 4-substituted-phenyl-cyclohexadiene-1,2-diacylate of (B) to form the corresponding 4'-substituted-3-acyloxybiphenyl and (D) effecting the hydrolysis of the 4-substituted-3-acyloxybiphenyl of (C) to produce the corresponding 4'-substituted-3-hydroxybiphenyl.

As taught by L. Nadim et al., Bacterial Oxidation of Polychlorinated Biphenyls, U.S. EPA Report #EPA/6500/9-87/015 P395-402, the oxidative pathway of biphenyl by *Alcaligenes eutrophus* NRRLB-15940, or *Pseudomonas putida* NRRLB-18064 is as follows:

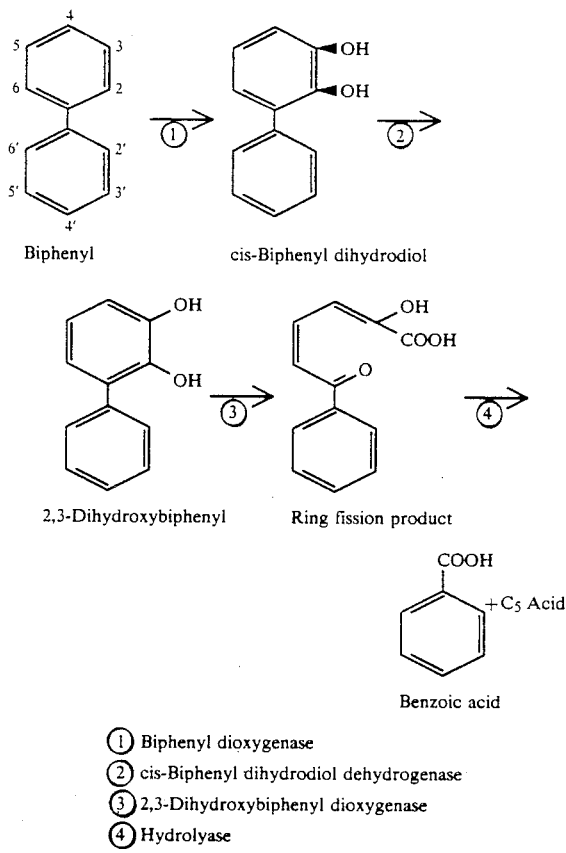

① Biphenyl dioxygenase
② cis-Biphenyl dihydrodiol dehydrogenase
③ 2,3-Dihydroxybiphenyl dioxygenase
④ Hydrolyase The mutagenesis of *Alcaligenes eutrophus* NRRLB-15940, more particularly shown in U.S. Pat. No. 4,843,007 and *Pseudomonas putida* NRRLB-18064, more particularly shown by Bopp in U.S. Pat. No. 4,843,009, is taught by Nadim et al. previously cited. There is used N-methyl-N'-nitro-N-nitrosoguanidine in accordance with the procedure of Finette et al., Isolation and Characterization of *Pseudomonas putida* PpFl Mutants Defective in the Toluene Dioxygenase Enzyme System, Journal of Bacteriology, vol. 160, No. 3, Dec. 1984, pp. 1003–1009 which is incorporated herein by reference. It was found, for example, that mutant organisms defective in cis-biphenyldihydrodiol dehydrogenase activity, as shown by step 2 in the above biphenyl pathway, could be produced utilizing the Finette et al. technique. It was discovered that 4-substituted biphenyls of formula (2) above, could be incubated with mutant organisms of *Alcaligenes eutrophus* NRRLB-15940, referred to hereinafter as "FM803" and *Pseudomonas putida* NRRLB-18064, referred to hereinafter as "FM408" to produce optically active (1S-cis)-3-(4-substituted-phenyl)-3,5-cyclohexadiene-1,2-diol of formula (3) above.

It has been found that optically active 4-substituted-phenylcyclohexadienediols of formula (3) can be acylated to form the corresponding 4-substituted-phenyl-3,5-cyclohexenediene-1,2-diacetate followed by treatment with base to selectively cleave the acetate group in the (2) position and proton in the (3) position to form the 4'-substituted-3-acetoxybiphenyl, followed by hydrolysis of the remaining acetate to form the 4-substituted-3-hydroxybiphenyl of formula (1).

Procedures for forming mutants is described in detail on page 1004 of Isolation and Characterization of *Pseudomonas Putida* PpFI Mutants Defective in the Toluene Dioxygenase Enzyme System, of Barry A. Finette et al. previously cited. These procedures of Finette et al. was used to form FM803 and FM408. Isolation of the FM803 and FM408 were achieved by the following procedure:

The strains were tested for their ability to grow using biphenyl (Bph+). Cells were plated onto a minimal medium containing 35 mg/l of 2,3,5-triphenyltetrazolium chloride and 0.02% succinate. Biphenyl was supplied as a vapor from crystals added to the lid of the plate. Cells unable to grow on biphenyl (Bph—) formed colonies which were small and colorless, while those able to grow on biphenyl produced larger colonies which were red in color. Dihydrodiol dehydrogenase deficient strains were identified by their ability to convert biphenyl to 2,3-dihydro-2,3-dihydroxybiphenyl in liquid culture. The product was initially identified spectrophotometrically by an absorbance maxima at 303 nm.

Incubation of the 4-substituted biphenyl, which preferably is 4-hydroxybiphenyl, can be achieved by initially forming a mixture of the 4-hydroxybiphenyl and the mutant strain, which hereinafter will mean either FM408 or FM803, in a minimal salts medium using L-Histidine as a carbon source. There can be used from 0.002 gm to 0.5 gm by weight of the 4-hydroxybiphenyl per 100 ml units of culture medium consisting of cells having an optical density at 615 nm of 0.2 to 10. The resulting incubation mixture can be agitated in a rotary shaking incubator at 20° to 37° C. for 1 to 72 hours. The culture broth can then be spun down in a centrifuge and filtered through a 0.45 micron filter. Recovery of the 4-substituted-biphenyldihydrodiol from the aqueous layer can be achieved by treating it with an aqueous solution of an alkali bicarbonate, such as sodium bicarbonate and sodium chloride, followed by extraction with a suitable solvent such as diethylether, followed by evaporation of the solvent after it has been properly dried.

Compounds of formula (3), where Y is hydrogen or hydroxy can be used as a synthetic intermediate for aromatic polymers and as an intermediate for making polymers such as polyesters and polycarbonates.

In order that those skilled in the art will be better able to practice the present invention, the following examples are given by way of illustration and not by way of limitation. All parts are by weight unless otherwise specified.

EXAMPLE 1

A culture of *Pseudomonas putida* NRRLB-18064 as shown by Bopp, U.S. Pat. No. 4,843,009, incorporated herein by reference, was grown to an optical density of 1.0 at 600 nm on Pseudomonas minimal media using biphenyl as the carbon source. A 10 ml portion of each culture was twice harvested by centrifugation and resuspended in an equal volume of Citrate Buffer (50 mM, pH 6.0). A solution of N-methyl-N'-nitro-N-nitrosoguanidine (7 mg/ml in 50 mM Citrate Buffer, pH 6.0) was added to a final concentration of 30 ug/ml. After mixing the cell suspensions were incubated at 30° C. for 39 minutes and then diluted and plated onto selective media to identify Bph— strains. FM408 was isolated in accordance with the Finette et al. procedure as described above.

The above procedure was repeated except that *Alcaligenes eutrophus* NRRLB-15940, as shown by Bedard, U.S. Pat. No. 4,843,007, which is incorporated herein by reference was substituted for the *Pseudomonas putida* strain. There was isolated FM803.

FM803 was grown in Pseudomonas Minimal Medium (500 ml) using 0.2% histidine as a carbon source. After the cell reached an optical density at 615 nanometers of 2.0, 0.1 gram (0.02%) of 4-hydroxybiphenyl was added to the culture. The culture was incubated at 30° C. in a rotary shaking incubator at 250 RPM. After 18-24 hours, the culture broth was spun down in a centrifuge and filtered through a 0.45 micron filter. There was added 2 grams/100 ml of sodium bicarbonate and 10 grams/100 ml of sodium chloride to the aqueous layer. The aqueous layer was extracted continually with diether ether for 12 hours. The ether layer was dried with sodium sulfate and concentrated. There was obtained a product which was purified via reverse-phase chromatography and characterized by UV spectroscopy, proton NMR spectroscopy and mass spectral analysis. Based on method of preparation and the aforementioned spectral data, the product was (1S-cis)-3-(4-hydroxyphenyl-3,5-cyclohexadiene-1,2-diol having the formula,

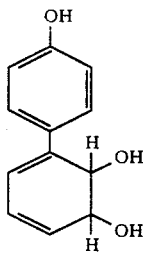

In a typical experiment, (1S-cis)-3-(4-hydroxyphenyl)-3,5-cyclohexadiene-1,2-diol was treated with excess acetic anhydride in pyridine as solvent at $-15°$ until HPLC indicated the absence of (1S-cis)-3-(4-hydroxyphenyl)-3,5-cyclohexadiene-1,2-diol in the reaction mixture. The reaction mixture was concentrated in vacuo and purified via chromatography on silica gel with 95/5 toluene/acetic anhydride as the eluent. Concentration yielded pure (1S-cis)-3-(4-acetoxyphenyl)-3,5-cyclohexadiene-1,2-diacetate, which was characterized via HPLC, UV spectroscopy, proton NMR spectroscopy and mass spectral analysis.

The above triacetate is useful as a synthetic intermediate for aromatic polymers and as an intermediate for making aromatic polyesters.

(1S-cis)-3-(4-acetoxyphenyl)-3,5-cyclohexadiene-1,2-diacetate in toluene at 10° C. was treated with five equivalents of DBU (1,8-diazabicyclo[5.4.0]undec-7-ene) to yield a mixture of products. The reaction mixture could be acetylated with excess acetic anhydride to yield a mixture of 99% 3,4'-diacetoxybiphenyl and 1% 2,4'-diacetoxybiphenyl. Alternatively, the reaction mixture could be hydrolyzed via treatment with ammonia saturated methanol to yield a mixture of 99% 3,4'-dihydroxybiphenyl and 1% 2,4'-dihydroxybiphenyl. The major products from these two reactions, 3,4'-diacetoxybiphenyl and 3,4'-dihydroxybiphenyl, are identical to authentic samples of these two compounds which were synthesized via traditional methods.

The above 3,4'-dihydroxybiphenyl and 2,4'-dihydroxybiphenyl and the corresponding acetates thereof are useful as synthetic intermediates for aromatic polymers and as intermediates for making aromatic polyesters and aromatic polycarbonate.

Although the above Example is directed to only a few of the very many variables which can be used in the practice of the method of the present invention and products obtained therefrom, it should be understood that the present invention is directed to the use of a broader variety of 4-substituted biphenyls and the synthesis of a much broader variety of hydroxylated 4-substituted biphenyls as set forth in the description preceding this example.

What we claim as new and desire to secure by Letters Patent of the United States is:

1. The compound (1S-cis)-3-(4-hydroxyphenyl)-3,5-cyclohexadiene-1,2-diol.
2. The compound (1S-cis)-3-(4-acetoxyphenyl)-3,5-cyclohexadiene-1,2-diacetate.

* * * * *